United States Patent [19]
Cline et al.

[11] Patent Number: 5,368,031
[45] Date of Patent: Nov. 29, 1994

[54] MAGNETIC RESONANCE SURGERY USING HEAT WAVES PRODUCED WITH A LASER FIBER

[75] Inventors: Harvey E. Cline; Thomas R. Anthony, both of Schenectady, N.Y.

[73] Assignee: General Electric Company, Schenectady, N.Y.

[21] Appl. No.: 125,520

[22] Filed: Sep. 24, 1993

Related U.S. Application Data

[62] Division of Ser. No. 751,259, Aug. 29, 1993, Pat. No. 5,291,890.

[51] Int. Cl.$^5$ ............................................. A61B 5/055
[52] U.S. Cl. ............................. 128/653.2; 128/653.5; 606/15; 606/28; 607/89; 607/96; 607/100; 607/113
[58] Field of Search ............... 128/653.1, 653.2, 653.5; 606/15, 28, 31; 607/88–89, 92, 96, 100, 102, 113

[56] References Cited

U.S. PATENT DOCUMENTS

| | | |
|---|---|---|
| 4,671,254 | 6/1987 | Fair . |
| 4,914,608 | 4/1990 | Lebihan et al. . |
| 4,950,267 | 8/1990 | Ishihara et al. ............... 606/15 |
| 4,951,688 | 8/1990 | Keren ............... 128/653.2 |
| 4,961,054 | 10/1990 | Park et al. . |
| 5,071,871 | 5/1991 | Mueller et al. . |
| 5,109,853 | 5/1992 | Taicher et al. ............... 128/653.2 |
| 5,131,392 | 7/1992 | Jolesz et al. ............... 128/653.2 |
| 5,187,658 | 3/1993 | Cline et al. . |
| 5,263,482 | 11/1993 | Leunbach ............... 128/653.2 |
| 5,284,144 | 2/1994 | Delannoy et al. ............... 128/653.2 |
| 5,291,890 | 3/1994 | Cline et al. ............... 128/653.2 |

FOREIGN PATENT DOCUMENTS 8907907  9/1989  European Pat. Off. .
3931854  4/1991  Germany .

OTHER PUBLICATIONS

"Mr Imaging of Laser-Tissue Interactions", by F. A. Jolez, et al., Radiology (1988), vol. 168, p. 249.
"Effects of Physical Parmeters on High Temperature Ultrsound Hyperthermia" by B. E. Billar, et al, Ultrasound in Med. & Biol. (1990), vol. 16, No. 4, pp. 409–420.
"Thermal Diffusity of Isotopically Enriched 12C Diamond" by T. R. Anthony, et al, Physical Review B, Jul. 15, 1990, vol. 42, No. 2, pp. 1104–1111.
"Conduction of Heat in Solids", H. S. Carlsow, et al, 2nd Edition, 1959, Oxford, Claredon Press, pp. 64–68.
"Temperature Mapping with Mr Imaging of Molecular Diffusion: Application to Hyperthermia", Radiology 1989, vol. 171, pp. 853–857.

Primary Examiner—K. M. Pfaffle
Attorney, Agent, or Firm—Lawrence P. Zale; Marvin Snyder

[57] ABSTRACT

Surgery is performed with pulsed heat means that selectively destroys tissue in a region within a patient. The size of the region destroyed is dependent upon the frequency of the pulses of the pulsed heat means and thermal conductivity of the tissue of the patient. The pulsed heat means can be a coherent optical source that is guided by laser fiber to the tissue to be destroyed. In another embodiment the pulsed heat means is a focussed ultrasound transducer that dissipates ultrasonic energy at a focal point within the region of tissue to be destroyed. A magnetic resonance imaging system employing a temperature sensitive pulse sequence creates an image of the tissue and the region being heated to allow a surgeon to alter the position of the pulsed heat means or vary the pulse frequency.

3 Claims, 4 Drawing Sheets

MAGNETIC RESONANCE SURGERY USING HEAT WAVES PRODUCED WITH A LASER FIBER

This application is a division, of application Ser. No. 07/751,259, now U.S. Pat. No. 5,291,890, filed Aug. 29, 1993.

BACKGROUND OF THE INVENTION

The present invention relates to surgery performed by local heating guided by magnetic resonance (MR) imaging methods of imaging, and more particularly to surgery performed by pulsed local heating guided by magnetic resonance (MR) imaging.

Conventional Magnetic Resonance Imaging (MRI) provides the radiologist with cross sectional views of the anatomy for diagnosis of pathology. MRI provides excellent contrast between different tissues and is useful in planning surgical procedures. A tumor is much more visible in an MR image than as seen in actual surgery because tumor and normal tissues often look similar in surgery. The tumor can also be obscured by blood during surgery. Researchers at Brigham and Womens Hospital, Boston, Mass. have proposed treatment of deep lying tumors by laser surgery. F. A. Jolesz, A. R. Bleire, P. Jakob, P. W. Ruenzel, K. Huttl, G. J. Jako, "MR Imaging of Laser-Tissue Interactions", Radiology 168:249 (1989). Thus, in the case of brain tumors, the patient is first scanned in an MRI system to locate the tumor and plan a safe trajectory between the entry and target points. This can be accomplished by a MRI device employing fast scan apparatus such as U.S. Pat. No. 4,961,054 Gradient Current Speed-up Circuit for High-speed NMR Imaging System by John N. Park, Otward M. Mueller, and Peter B. Roemer, issued Oct. 2, 1990, or U.S. Pat. No. 5,017,871 Gradient Current Speed-up Circuit for High-speed NMR Imaging System, by Otward M. Mueller, and Peter B. Roemer, issued May 21, 1991 both assigned to the present assignee and hereby incorporated by reference. A small burr hole is drilled in the skull and a hollow needle containing an optical fiber is then inserted into the tumor. The patient is then placed back into the MRI system to view the region heated by the laser using a temperature sensitive pulse sequence. Temperature Sensitive pulse sequence is described in U.S. Pat. No. 4,914,608 In-vivo Method for Determining and Imaging Temperature of an Object/Subject from Diffusion Coefficients Obtained by Nuclear Magnetic Resonance, Denis LeBihan, Jose Delannoy, and Ronald L. Levin issued Apr. 3, 1990 and hereby incorporated by reference. Experiments on animals show that a heated zone above a critical temperature destroys tissue. This zone increases in size with time as the heat is applied to reach a steady state or both temperature and heat flow. If the maximum temperature is limited to 100 deg. C, then the laser heated zone, the area exceeding a critical temperature causing destruction of tissue, approaches 1 centimeter in diameter. It is difficult to predict the heated zone geometry because the heat flow depends on the profusion of blood as well as the tissue thermal properties.

Tumors have been selectively destroyed in cancer patients using focussed ultrasound heating at the University of Arizona, B. E. Billard, K. Hynynen and P. B. Roemer Effects of Physical Parameters on High Temperature Ultrasound Hyperthermia Ultrasound in Med. & Biol. Vol. 16, No. 4, pp. 409–420, 1990 hereby incorporated by reference. Billard et al. disclosed that the control of heat was improved by using short laser pulses where the effect of blood perfusion is negligible. However, since they did not image the temperature distribution, it was difficult to hit small, deep laying targets.

It would be beneficial to be able to accurately localize heat to selectively kill or destroy tumor tissue without damage to surrounding healthy tissue.

OBJECTS OF THE INVENTION

It is an object of the present invention to selectively destroy tumors accurately with a non-invasive procedure employing the use of magnetic resonance imaging, and focussed ultrasound.

It is another object of the present invention to selectively destroy tumors accurately with a small degree of invasiveness employing the use of magnetic resonance imaging, and a pulsed laser.

SUMMARY OF THE INVENTION

Pulsed heat is used to selectively destroy tumor tissue of a patient with a minimum amount of surgery. Magnetic resonance (MR) imaging is employed to provide to a surgeon performing the procedure images of a region within the patient being heated, such region including the the tumor tissue. A series of fast scan MR images are used to monitor the temperature with a diffusion sensitive pulse sequence. The pulsed heat is received by the tumor tissue in the form of coherent optical energy produced by a laser and guided through optical fiber to a hollow needle placed into the tumor. Another embodiment employs a focussed ultrasound transducer as the heat source with the heat concentrated at a focal point. The heat is localized by adjusting the frequency of the pulses, since an oscillating point heat source creates a heat wave that decays exponentially with distance from the source with a decay rate determined only by the frequency. The needle or focal point is positioned by a mechanical guide under the control of the surgeon.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
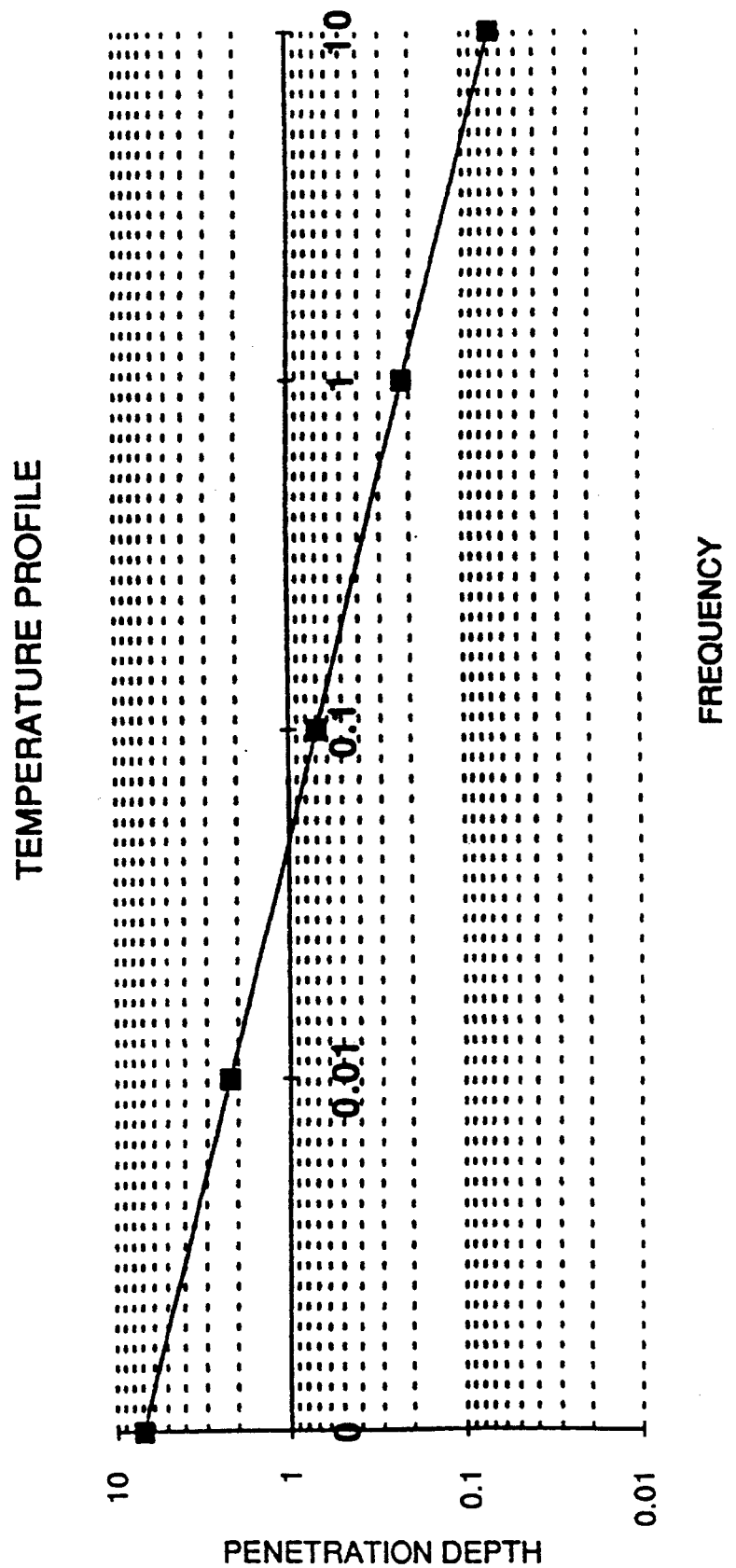
FIG. 1 is a logarithmic graph of Frequency vs. heat Penetration Depth of a pulsed heat means according to the present invention.

By employing the present invention, tumor tissue in a patient can be selectively destroyed by localized heating without affecting the surrounding healthy tissue. A method of selectively heating material such as diamond is disclosed in Thermal Diffusity of Isotopically Enriched $^{12}C$ Diamond by T. R. Anthony, W. F. Banholzer, and J. F. Fleischer Phys. Rev. B Vol. 42, No. 2 Jul. 15, 1990 hereby incorporated by reference. The source of the heat may be either a focussed ultrasound transducer or a laser source routed to the tumor tissue through an optical fiber. The heat is applied to the tumor tissue in a pulsed or oscillating fashion. This oscillation creates a heat wave either at the tip of the optical fiber or at the focus point of the transducer. The pulsed heat is produced by a source driven in accordance with a sinusoidal component and a constant component, and thus varies sinusoidally. Although the sinusoidal component of the applied heat would imply a negative heating or heat withdrawal, the constant heat term added to the sinusoidal component keeps the heat flow positive. However, the constant heating from a point source steadily adds to the background thermal distribution. The temperature distribution T may be expressed as T(r, t) with r being the radius from the center of the point of application, and t being time. The temperature distribution satisfies the diffusion equation:

$$D\nabla^2 T(r,t) + dT(r,t)/dt = Q(r,t)/\rho c \qquad [1]$$

where $\omega$ is an angular frequency,
$\rho$ is the density of the heated tissue,
c is the specific of the heated tissue
and D is the thermal diffusity of the heated tissue.

In the case of a periodic point heat source of amplitude $Q_0$ at the origin $r=0$, the heat flow becomes:

$$D\nabla^2 T(r,t) + dT(r,t)/dt = (Q_0/\rho c) Cos(\omega t) \delta(r) \qquad [2]$$

with frequency $f = \omega/2\pi$. A radially symmetric solution is of the form:

$$T(r,t) = Q/\rho c \, Exp[-kr] cos(\omega t - kr)/r \qquad [3]$$

where $k = Sqrt[\omega/2D]$, and D is the thermal diffusity. The wavelength $L = 2\pi/k$ of heat waves depends on the thermal diffusivity D and frequency f, so that $$T(r,t) = Q/\rho c \, Exp[-kr] cos(2\pi f t - kr)/r \qquad [4]$$

The heat from an oscillating point source decays exponentially with a characteristic distance $1/k$ as shown in H. S. Carlsow and J. C. Jaeger Conduction of Heat in Solids 2nd Edition, Oxford, Clarendon Press, 1959 at pages 64–70 hereby incorporated by reference. The heat decay is given by:

$$\begin{aligned} 1/k &= Sqrt[2D/\omega] \\ &= Sqrt[D/\pi f] \end{aligned} \qquad [4]$$

The frequency of the oscillating point source is controlled to vary the size of the heated region. The size of the heated region can be seen with the use of a Magnetic Resonant (MR) imaging system employing a temperature sensitive MR pulse sequence. The MR imaging system also creates an image of the tissue intended to be destroyed. By varying the frequency of the oscillating point source, the surgeon can selectively destroy a small region of tissue, thus performing non-invasive micro surgery. The operator of the apparatus, such as a surgeon, can adjust the placement of the oscillating point source and the size of tissue destroyed while monitoring the images of the heated tissue and the tumor. In an alternative embodiment, the frequency of the oscillating source and the placement of the oscillating point source of heat are under the control of a mechanical guide responsive to the MR temperature sensitive fast scan imaging system.

Consider heat applied at a point by either a laser fiber or focussed ultrasound transducer. The heat may be applied over a spot of up to 1 mm. in radius because of the laser optical absorption or diffraction limit of focussed ultrasound. The thermal diffusivity D of tissue is similar to that of water, which is 0.0015 cm²/sec. The penetration depth for a given frequency f is tabulated below

TABLE 1

| FREQUENCY (Hz) | PENETRATION DEPTH (mm) |
|---|---|
| 0.001 | 6.9 |
| 0.01 | 2.2 |
| 0.1 | 0.69 |
| 1 | 0.22 |
| 10 | .069 |

The temperature profile decays exponentially with distance from the oscillating heat source with a penetration depth that, as evident from Table 1, depends on the frequency. FIG. 1 is a logarithmic graph of Frequency vs. Penetration Depth.

Figure 2:
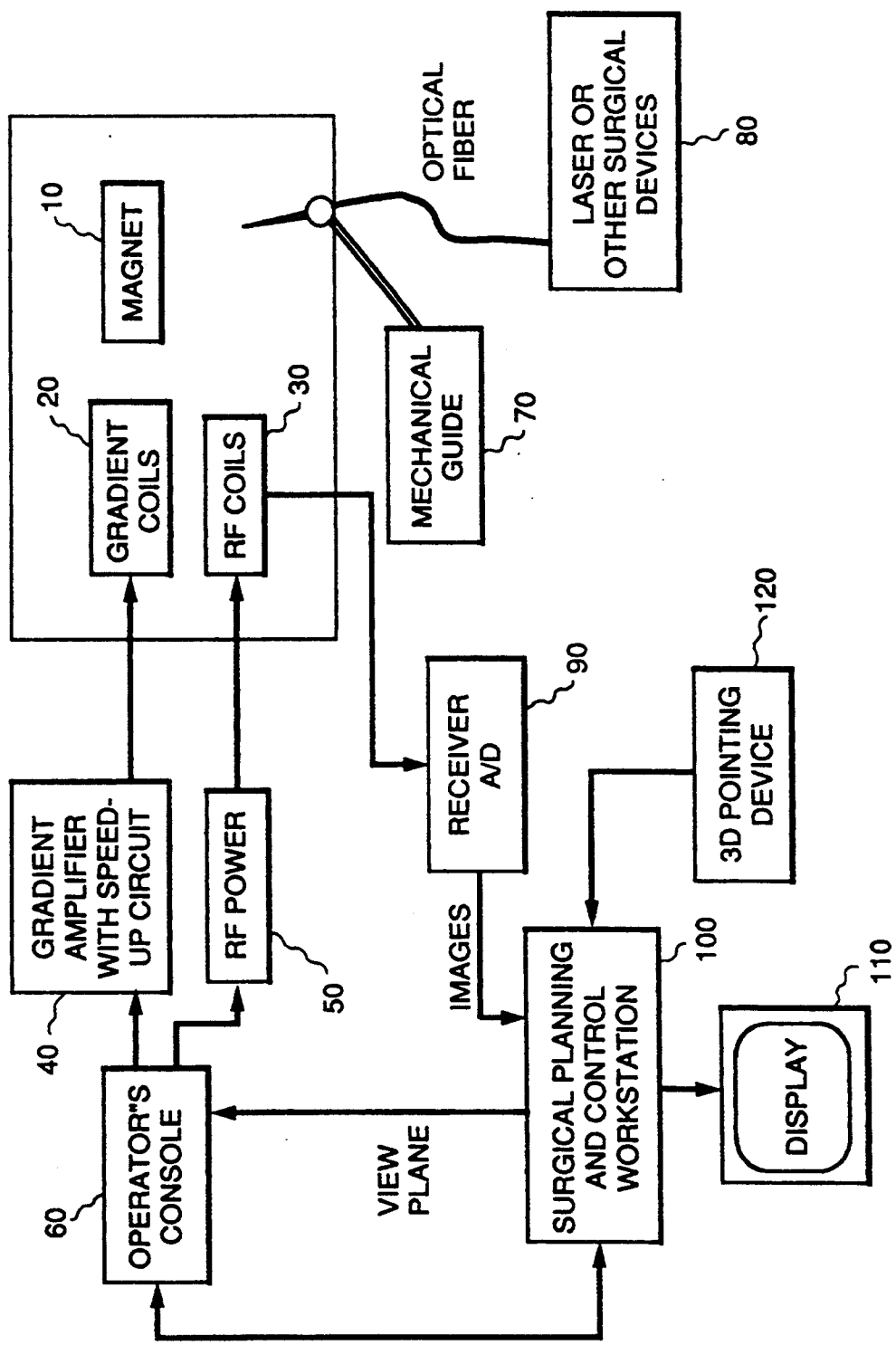
FIG. 2 is a schematic block diagram of one embodiment of the present invention.

A schematic block diagram of the magnetic resonance surgery system is shown in FIG. 2. A magnet 10 provides a uniform field for nuclear magnetic resonance imaging using both gradient coils 20 and radiofrequency (RF) coils 30 to detect the resonance of protons in the patient. A pulse sequence is applied to the coils by gradient amplifier 40 and RF power source 50 to the coils to acquire temperature sensitive images rapidly during surgery. Operator's console 60 is used to control the imaging. A mechanical guide 70 positions the laser fiber or ultrasound transducer 80. Raw data is sent from receiver 90 to a surgical planning and control workstation 100 that displays images 110 to the surgeon and enables him to guide the heat source by means of a three-dimensional (3D) pointing device 120 such as a track ball or a mouse.

Figure 3:
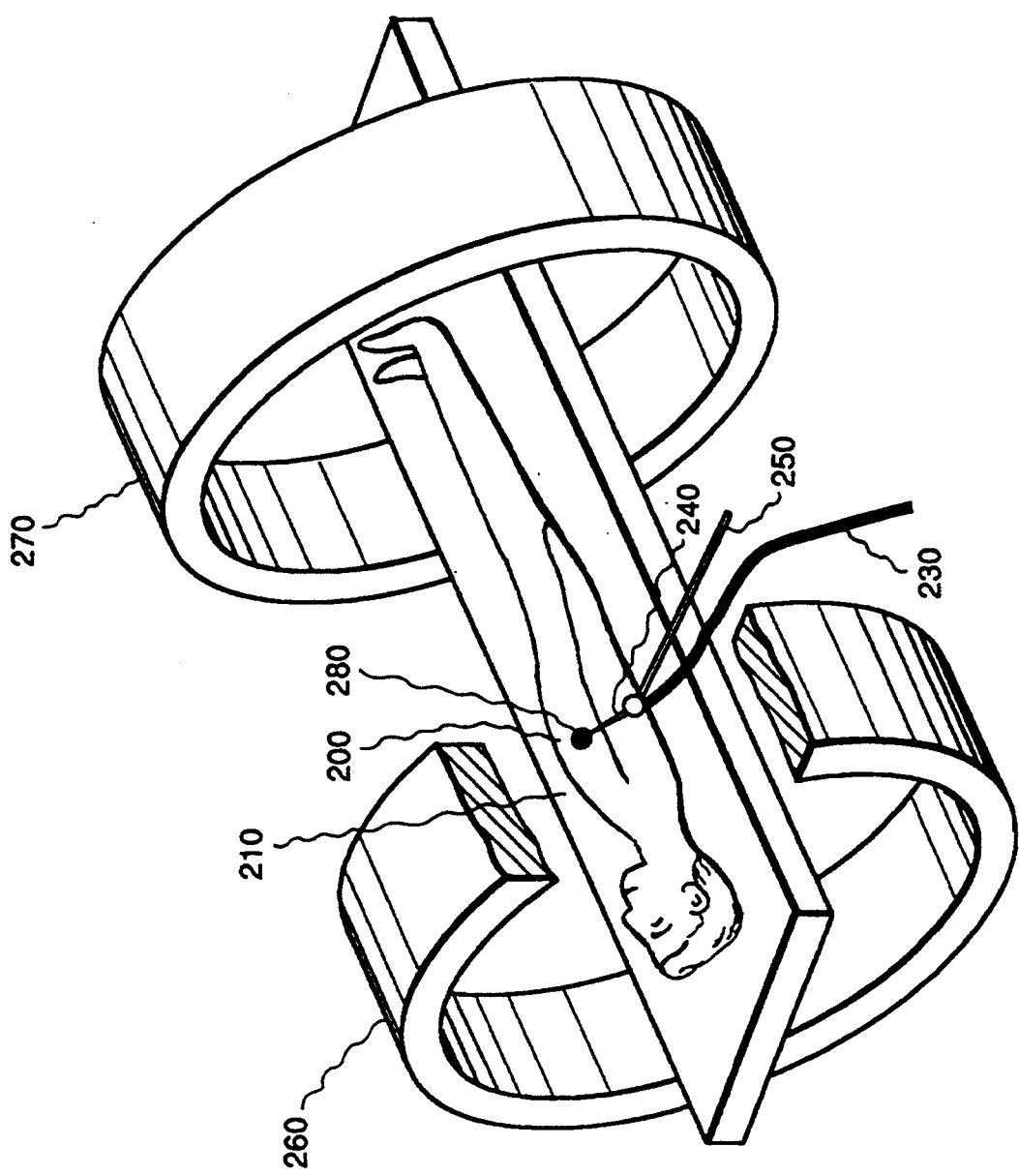
FIG. 3 is a partial perspective view of a patient positioned for surgery within the bore of the magnets of one embodiment of the present invention employing a laser source and fiber optics.

As shown in FIG. 3, a patient 200 lies on a table 210 that moves into the bore of a two part magnet 260, 270. A laser fiber 230 is inserted into the patient with a hollow needle 240 guided by a mechanical positioning device 250 such as a hydraulic positioner. The trajectory is computed from a set of images of the patient taken during surgery planning. A safe trajectory from the entry point to the target does not intersect critical anatomy such as large blood vessels. Heat is applied to tumor tissue 280 by periodically pulsing the laser through laser fiber 230 (i.e., a fiber optic material) to selectively destroy tumor 280 while the operator views a temperature sensitive magnetic resonance image. More than one needle may be required to remove an irregular shaped tumor.

An alternative embodiment (not shown) may employ a heat source that creates heat over a line segment instead of a point.

Figure 4:
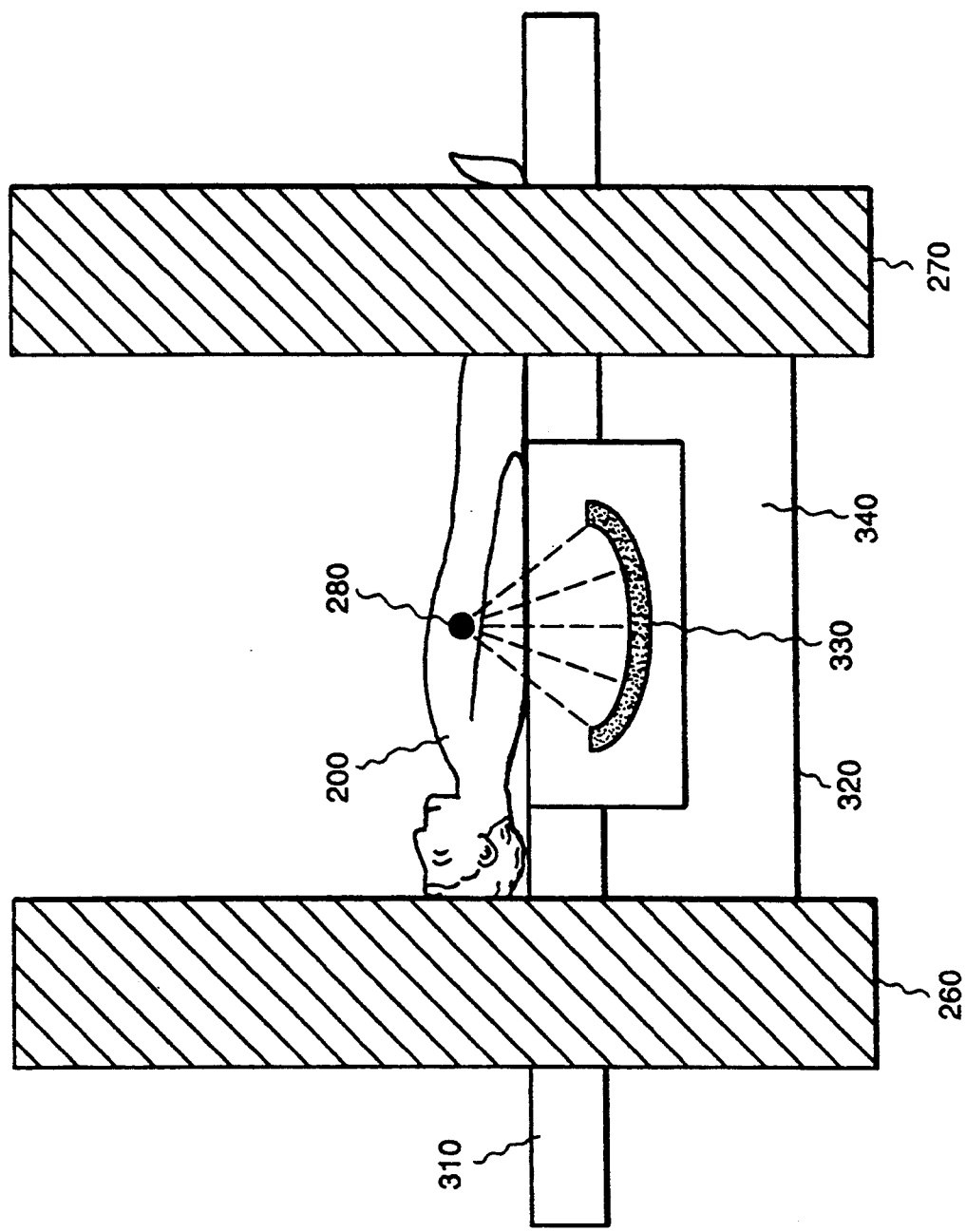
FIG. 4 is a partial view of a patient positioned for surgery within the bore of the magnets of another embodiment of the present invention employing a focussed ultrasound source.

As shown in FIG. 4, patient 200 is placed on a table 310 designed to accommodate a focussed ultrasound transducer 330 in a water bath 320. The ultrasound transducer 330 can be moved inside the bore of magnets 260, 270 to focus on different locations within patient 200. Ultrasound transducer 330 is focussed onto the tumor tissue 280, avoiding bone or air in the path of the ultrasound beam, and pulsed to selectively heat tumor tissue 280 at the focal point of the ultrasound transducer. The ultrasound transducer is moved while the surgeon views cross sectional temperature sensitive images.

While several presently preferred embodiments of the invention have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) surgery system that comprises:
  a) an invasive device having a tip adapted for being inserted into a patient, the invasive device capable of transmitting optical energy at an application point proximate to the tip;
  b) an optical source for applying heat waves by pulsing optical energy through the tip of the invasive device at a frequency f and amplitude Q at the application point to create a heated region having a temperature distribution T(r,t) around the application point described by:

$$T(r,t) = Q/\rho c\, Exp[-kr]\cos(2\pi ft - kr)/r \qquad [4]$$

where Q is the amplitude of heat provided;
  r is the radius from the center of the heated region;
  t is time;
  $\rho$ is density of the heated region;
  c is specific heat of the heated region; and
  k = Sqrt ($\omega$/2D), where D is the thermal diffusity of the tissue in the heated region;
  c) MR compatible positioning means, connected to the invasive device, for positioning the tip of the invasive device such that the application point is positioned to cause a selected tissue within the patient to have the desired temperature distribution T(r,t);
  d) an MR imaging means adapted for creating fast scan MR images of the temperature distribution T(r,t) around the application point during surgery using a temperature sensitive pulse sequence; and
  e) display means, coupled to the MR imaging means, for interactively displaying the temperature sensitive images to an operator to allow the operator to control the temperature distribution T(r,t).

2. The MR surgery system of claim 1 wherein the optical source comprises a laser.

3. A method of performing heat surgery on a patient, as guided by a magnetic resonance (MR) imaging apparatus capable of producing temperature sensitive MR images, comprising the steps of;
  a) determining a position of a selected tissue to be destroyed in said patient with said MR imaging apparatus,
  b) positioning a tip of an optical fiber at an application point near the selected tissue within said patient;
  c) determining a desired temperature distribution T(r,t);
  d) pulsing optical energy at a frequency f and amplitude Q in order to create a heated region having the desired temperature distribution around the application point, such that:

$$T(r,t) = Q/\rho c\, Exp[-kr]\cos(2\pi ft - kr)/r \qquad [4]$$

where Q is the amplitude of heat provided;
  r is the radius from the center of the heated region;
  t is time;
  $\rho$ is density of the heated region;
  c is specific heat of the heated region; and
  k = Sqrt ($\omega$/2D), where D is the thermal diffusity of the tissue in the heated region;
  e) monitoring the temperature distribution T(r,t) with said MR imaging apparatus; and
  f) adjusting the frequency f, the amplitude Q and the location of the application point.

* * * * *